United States Patent

Carmen et al.

Patent Number: 5,721,024
Date of Patent: Feb. 24, 1998

[54] MATERIAL FOR FLEXIBLE MEDICAL PRODUCTS

[75] Inventors: Raleigh A. Carmen, Fullerton; Ronald H. Bauman, Arcadia, both of Calif.

[73] Assignee: Pall Corporation, East Hills, N.Y.

[21] Appl. No.: 487,493

[22] Filed: Jun. 7, 1995

[51] Int. Cl.$^6$ .................................................. A61J 1/05
[52] U.S. Cl. ....................... 428/35.2; 428/35.4; 428/35.5; 428/35.7; 428/36.6; 604/403; 604/408; 604/410; 422/40; 422/41; 526/344.3
[58] Field of Search ................ 428/35.2, 35.4, 428/35.5, 35.7, 36.6; 604/403, 408, 410; 524/296, 297, 145, 310, 311; 526/344.3; 422/40, 41

[56] References Cited

U.S. PATENT DOCUMENTS

| | | | |
|---|---|---|---|
| 4,222,379 | 9/1980 | Smith | 128/214 |
| 4,280,497 | 7/1981 | Warner et al. | 128/272 |
| 4,313,866 | 2/1982 | Renshaw | 260/31.8 |
| 4,507,119 | 3/1985 | Spencer | 604/280 |
| 4,586,928 | 5/1986 | Barnes et al. | 604/408 |
| 4,596,657 | 6/1986 | Wisdom | 210/206 |
| 4,670,013 | 6/1987 | Barnes et al. | 604/403 |
| 4,710,532 | 12/1987 | Hull et al. | 604/408 |
| 4,810,378 | 3/1989 | Carmen et al. | 210/206 |
| 4,943,287 | 7/1990 | Carmen | 604/408 |
| 5,100,564 | 3/1992 | Pall et al. | 210/782 |
| 5,191,007 | 3/1993 | Zelazny et al. | 524/336 |

FOREIGN PATENT DOCUMENTS

| | | |
|---|---|---|
| 1280248 | 2/1991 | Canada. |
| 0411429 | 2/1991 | European Pat. Off.. |
| 1412994 | 11/1975 | United Kingdom. |
| 8702684 | 5/1987 | WIPO. |

OTHER PUBLICATIONS

Carmen, R., "The Selection of Plastic Materials for Blood Bags," *Transfusion Medicine Reviews* 7(1):1–10 (Jan. 1993).

Patterson & Dunkelberger, "Review of Literature and Resin Manufacturer Molecular Weight–Viscosity Relationships for PVC," *J. Vinyl & Additive Tech.* 1(1):21–25 (Mar. 1995).

*Primary Examiner*—Rena Dye
*Attorney, Agent, or Firm*—Leydig, Voit & Mayer, Ltd.

[57] ABSTRACT

Improved flexible film and tubing for medical products manufactured from a PVC compound, comprising an amount of ultra high molecular weight (UHMW) PVC resin having an inherent viscosity ranging from about 1.25 to about 2.00, most preferably about 1.71, and about 43 to about 57 percent by weight of a medically acceptable plasticizer, most preferably about 53 percent, such as tri (2-ethylhexyl) trimellitate (TOTM).

20 Claims, 3 Drawing Sheets

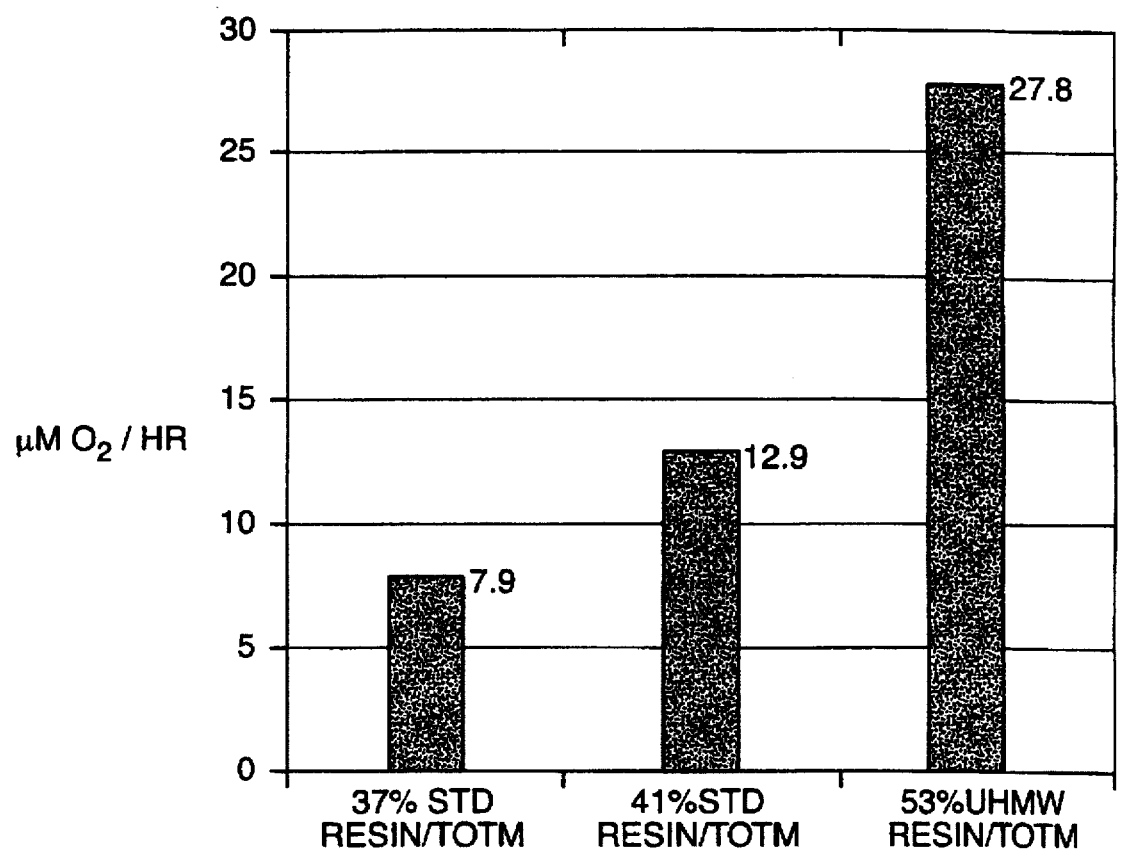
FIG._1

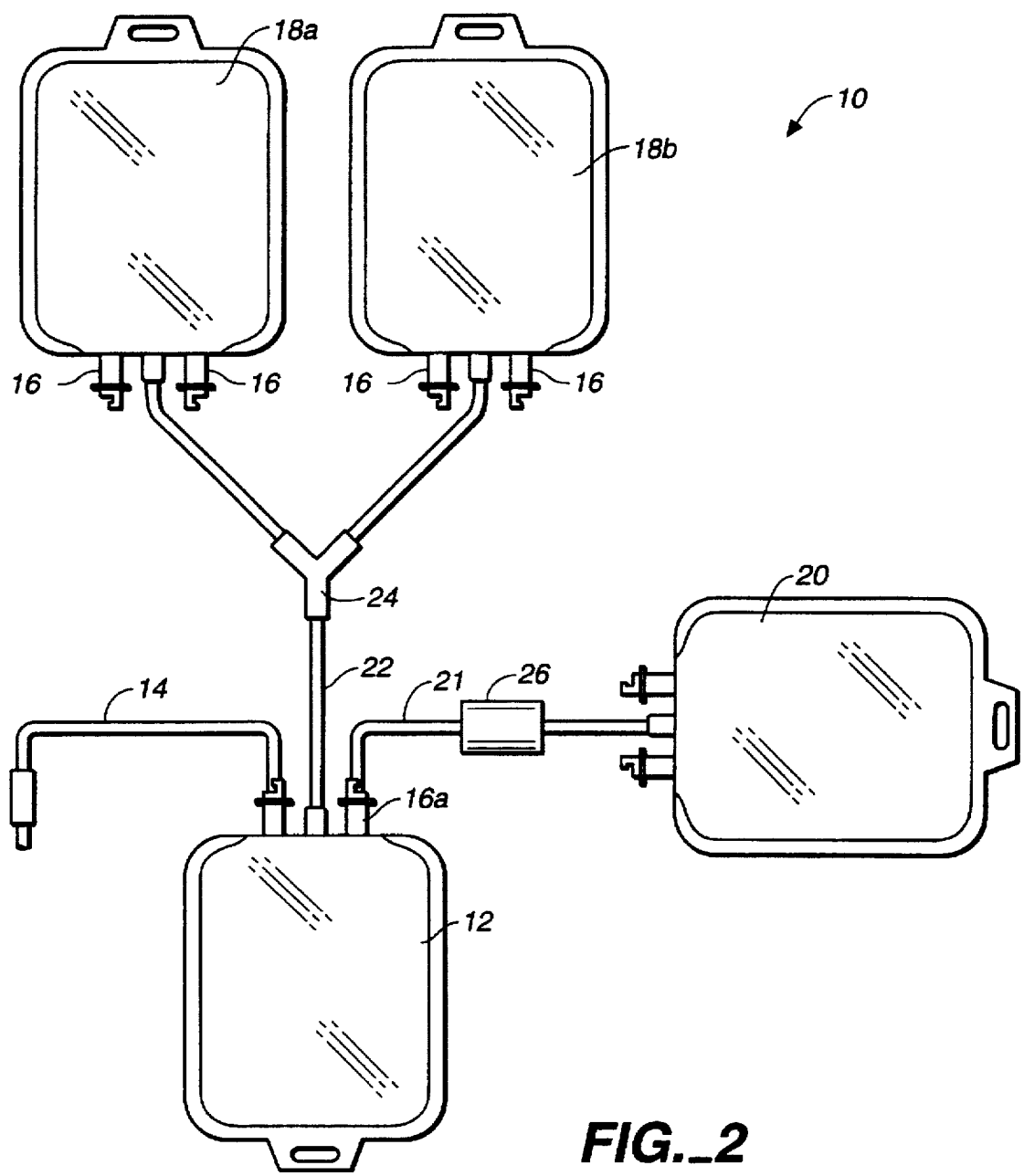
FIG._2

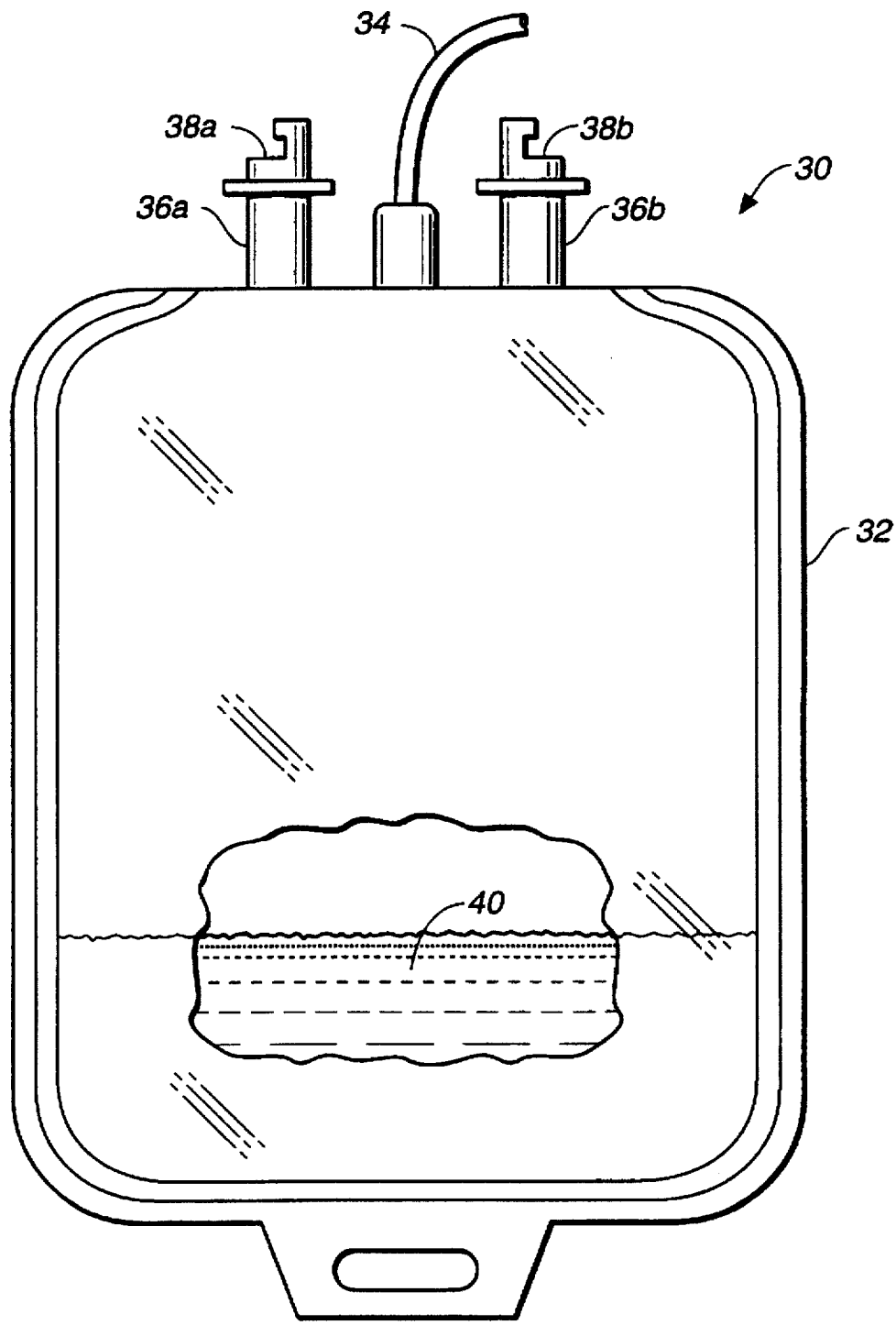
FIG._3

MATERIAL FOR FLEXIBLE MEDICAL PRODUCTS

TECHNICAL FIELD

The present invention generally relates to novel materials for manufacturing flexible medical products. The invention particularly relates to a novel PVC compound that may be used to manufacture plastic film and tubing used to make a variety of blood bags.

BACKGROUND OF THE INVENTION

Flexible plastic blood bags first replaced glass bottles for collecting blood as early as the late 1940's. Although blood bags have been manufactured from a variety of plastics materials and films, by 1955, the preferred material used for manufacturing flexible plastic blood bags was polyvinyl chloride (PVC) mixed with a plasticizer.

PVC is a polymerized form of the monomer vinyl chloride. Since polymers generally are of little value alone, they must be compounded with various additives to make useful material, or plastic. This particularly is true of PVC plastic. Alone, PVC is a hard and rigid substance and cannot be used to make articles, particularly not blood bag film. PVC must be plasticized with any one of several plasticizers to provide flexibility. In addition, PVC is heat-sensitive, thus a stabilizer must be added to prevent degradation of the polymer at the high temperatures required to melt the polymer and form the desired article, such as a film or tubing.

There are several classes of polymeric materials currently available in addition to PVC, including polyethylene, poly (vinylidene chloride), polycaprolactam, and polyisoprene. Each class includes hundreds of different compounds, making thousands of plastics available for use in manufacturing various articles. However, the use of these other materials for manufacturing certain medical articles, such as blood bags, which come in direct contact with body fluids and the like that are reintroduced into the body, is limited by medical and regulatory requirements. PVC has the desired properties for manufacturing film of the type that is used to produce blood bags.

Specifically, the plastic film must be flexible to permit not only filling during blood collection, but also to permit transfer of the blood components by expression and complete emptying by transfusion. Flexible, pliable material also facilitates centrifugation to separate out the various blood components if desired. The film must be capable of withstanding both extremely high temperatures (e.g., 115° C.–120° C.) and extremely low temperatures (e.g., –70° C.), since blood bags must be autoclaved (i.e., sterilized using high-pressure steam), and may be subject to freeze-fracturing to remove blood components.

In addition to use considerations, plastic film used for manufacturing medical articles, such as blood bags, must satisfy certain constraints imposed by the manufacturing process. Manufacturing closed containers from plastic film, such as blood bags, requires that certain edges hold a seal that can withstand the rigors of handling discussed above. Methods for sealing include heat sealing, radio-frequency (RF) sealing, and chemical bonding, among others. RF sealing is preferred for blood bags, but requires that the plastic material have a certain degree of polarity.

As mentioned above, PVC must include a plasticizer to give the otherwise rigid material the desired qualifies, including flexibility. Almost since its discovery as a viable polymer for use in manufacturing medical articles, the plasticizer of choice for PVC blood bags has been di (2-ethylhexyl) phthalate (DEHP). Other well-known medically acceptable plasticizer materials include tri (2-ethylhexyl) trimellitate (TOTM) and, more recently, citrate esters.

It has been reported by various sources since the early 1970's that DEHP plasticizer is lipophilic and tends to extract into blood components stored in blood bags manufactured from PVC/DEHP film. Although U.S. Pat. No. 4,222,379 to Smith described the extraction of DEHP as beneficial for the long term storage of red blood cells (RBCs), concern has been expressed about the potential deleterious effects of using such extractive plasticizers since, over a period of time, considerable amounts of them can collect in blood and blood components. For example, it has been reported that eluted DEHP inhibits the coagulation ability of platelets.

The leaching of DEHP from DEHP-plasticized PVC spurred development of non-leaching plasticizers. TOTM is one of the most commonly used non-extracting plasticizers. Its use as a PVC plasticizer in blood bags is described in detail in U.S. Pat. No. 4,280,497 to Warner et al.

High gas transmission is a desired feature of films from which blood bags used for storing platelets are manufactured, because gas transmission, particularly oxygen transmission, helps to overcome deleterious pH changes that naturally occur with blood components stored for extended periods of time. Warner et al. suggests that the amount of TOTM plasticizer in the PVC used to make blood bag film should range from about 30 to about 50 weight percent, preferably about 37 weight percent.

Since TOTM was found to be responsible for higher gas transmission, further attempts were made to increase gas transmission of plastic films used in the manufacture of blood bags by increasing TOTM content in the plastic. Currently, such improved commercially available blood bags typically have about 41 percent by weight TOTM in the PVC film. Amounts of TOTM greater than 41 percent are not adequately absorbed in the existing resin compounds and the resulting film product is both tacky and unmaleable.

Unfortunately, the upper limit of about 41 percent TOTM limits increased gas transmission in blood bags manufactured from such plastic film. This, in turn, limits the maximum storage duration of blood components, such as platelets, and the quantities of blood components that may be stored in a plastic blood bag of a given size.

In the years since the work leading to the Warner et al. patent, developments have been made in the art of PVC formulation that have resulted in a wide variety of medical applications for films manufactured from PVC. For example, one method for increasing gas transmission has been the use of alternate plasticizers, such as the citrate-based plasticizers disclosed in Canada patent 1,280,248 to Mahal. n-butryl tri-n-hexyl citrate (BTHC) now is used in manufacturing plastic films having high gas transmission. However, when used to manufacture platelet blood bags, the BTHC has higher leaching from the PVC than other plasticizers and, like DEHP, is not considered to be suitable for films used for platelet storage bags because of its coagulation inhibition effect. There have been reports that platelets stored for seven days in PVC/BTHC bags contain up to 400 ppm BTHC.

Thus, there remains a need for a plastic compound that has high gas transmission, specifically high oxygen transmission, and that otherwise is suitable for being formed into rims and tubing to be used in medical devices and applications.

SUMMARY OF THE INVENTION

In accordance with the present invention there is provided an improved flexible film and tubing that comprises a PVC compound, comprising an mount of ultra high molecular weight (UHMW) PVC resin having an inherent viscosity (logarithmic viscosity number, as defined by ASTM D-1243) ranging from about 1.25 to about 2.00 and about 43 to about 57 percent by weight of a medically acceptable plasticizer, such as tri (2-ethylhexyl) trimellitate (TOTM).

In a preferred embodiment, the UHMW PVC resin has an inherent viscosity of about 1.71 and contains about 50 weight percent plasticizer most preferably about 53 weight percent. The novel film manufactured from the PVC compound may be used to manufacture flexible containers for blood and blood components having an oxygen transmission that is at least 50% higher than that of prior art containers.

In a preferred embodiment, a plasticizer is chosen that extracts relatively small mounts of the plasticizer into blood components stored in blood bags manufactured from the UHMW PVC films.

BRIEF DESCRIPTION OF THE DRAWINGS

FIG. 1 is a bar graph showing the relative gas transmission of: (i) a prior art standard TOTM plasticized PVC bag of Warner et al. (37% standard PVC resin/TOTM); (ii) the current commercially available product (41% standard PVC resin/TOTM), available from Bayer Corporation, having a slightly elevated amount of plasticizer; and (iii) blood bags manufactured from a film embodying the present invention herein disclosed (53% ultra high molecular weight PVC resin/TOTM).

FIG. 2 illustrates a plan view of a multiple blood bag system which employs at least one blood bag manufactured using a PVC film embodying the present invention.

FIG. 3 is a partial cut-away plan view of a plastic container manufactured using a PVC film embodying the present invention.

DETAILED DESCRIPTION OF PREFERRED EMBODIMENTS

The present invention is an improved PVC compound that may be made into flexible plastic film and tubing used to manufacture medical products. The film and tubing are manufactured from the novel polymer compound that includes an ultra high molecular weight polyvinyl chloride (PVC) resin, mixed with an amount of a plasticizer in the range of about 43% to about 57%, which plasticizer does not leach in biologically significant amounts from the polymer film under certain use conditions.

The novel plastic film preferably has the qualities of: (1) flexibility, to permit the film to be formed and sealed in a variety of shapes and products, such as containers and tubing used in the medical and related industries; (2) pliability, to enable the products manufactured from the film to withstand extreme forces, such as centrifugation, without losing form; (3) resilience to temperature fluctuations, so the film can withstand both high temperatures during sterilization processes and low temperatures during freezing for storage or other processing; and (4) high gas transmission, specifically high oxygen transmission. In addition, it is preferable that the plasticizer does not significantly leach out of the plastic compound, either in film or tubing form, and into contacting fluids during use.

One standard method of identifying PVC resins in the industry is by the molecular weight of the resin. Another method, and the one commonly used in PVC polymer chemistry, is by dilute solution viscosity measurements. Essentially, this identification method measures the flow of a dilute solution of PVC resin and a pure solvent through a viscometer. The results may variously be calculated under different conditions of solvent concentration and temperature as K value, relative viscosity, intrinsic viscosity, and inherent viscosity. The use of these viscosity references under the exact same test conditions, is a useful method of relating one polymer to another.

These terms are defined by the American Society of Testing and Materials (ASTM) in ASTM D-1243. Specifically, "relative viscosity" is defined as the ratio of flow time of a solution of a polymer (0.2±0.002 of polymer in 100 ml solvent) to the flow time of a pure solvent. The International Union of Pure and Applied Chemistry (IUPAC) term for relative viscosity is "viscosity ratio". "Specific viscosity" is defined as relative viscosity minus one. Specific viscosity represents the increase in viscosity that may be attributed to the polymeric solute. "Reduced viscosity" is defined as the ratio of specific viscosity to the concentration. Reduced viscosity is a measure of the specific capacity of the polymer to increase the relative viscosity. "Inherent viscosity" is defined as the ratio of the natural logarithm of the relative viscosity to the concentration. The IUPAC term for inherent viscosity is logarithmic viscosity number. "Intrinsic viscosity" is defined as the limit of the reduced and inherent viscosities as the concentration of the polymeric solute approaches zero and represents the capacity of the polymer to increase viscosity. Interactions between solvent and polymer molecules have the affect of yielding different intrinsic viscosities for the same polymer in various solvents. The IUPAC term for intrinsic viscosity is limiting viscosity number.

Briefly, the method used to determine dilute solution viscosity involves taking a sample of resin is dissolved in cyclohexanone to make a solution of specified concentration. Inherent viscosity (logarithmic viscosity number) is calculated from the measured flow times of the solvent and of the polymer solution. Relative and inherent viscosity (viscosity ratio and logarithmic viscosity number) are calculated based on the following respective formulae:

$$\eta_{rel} = t/t_o \qquad (1)$$

$$\eta_{inh} = (\ln \eta_{rel})/C \qquad (2)$$

wherein:

$\eta_{rel}$ represents relative viscosity (viscosity ratio), t represents efflux time of the solution, $t_o$ represents efflux time of the pure solvent, C represents weight of sample used per 100 milliliter of solvent, $\eta_{inh}$ represents inherent viscosity (logarithmic viscosity number), and $\ln \eta_{rel}$ represents natural logarithm of relative viscosity (viscosity ratio). In general, the higher the inherent viscosity, the more plasticizer that can be absorbed by the resin particles, thereby permitting fabrication of higher plasticizer, increased gas transmission films.

High inherent viscosity PVC resins also are referred to as ultra high molecular weight (UHMW) PVC resins. Thus, UHMW PVCs may be defined as PVCs having an inherent viscosity above about 1.25, typically as high as about 2.00.

The plastic used in manufacturing the PVC compound of the present invention preferably is an ultra high molecular weight PVC resin. Such resins are commercially available from Occidental Chemical Corp., Vinyls Division, Dallas, Tex., and have the typical properties set forth in Table 1 below.

TABLE I

| Property | Range |
|---|---|
| Inherent Viscosity (ASTM D-1243) | 1.25–1.71 |
| Relative Viscosity (1% Solution in Cyclohexane @25° C.) | 2.80–4.00 |
| K Value (DIN 53726) | 78–93 |
| Specific Gravity (ASTM D-792) | 1.4 |
| Bulk Density (gm/cc) (ASTM D-1895) | 0.49–0.43 |
| Particle Size Distribution: | |
| (ASTM D-1921/OCC Test 510) | |
| % Retained, 40 Mesh | 0 |
| % Through, 200 Mesh | 10–5 |
| Plasticizer Sorption (ASTM D-1755) | 110–135 |
| Volatiles, % (OCC Test 260) | 0.3 |

The UHMW PVC resins of the type described above, have about 0.3% volatiles. The above property values represent approximate values, actual values may fluctuate depending on the particular batch composition for each resin.

Using such UHMW PVC resin enables the production of film sheets having about 100% improved gas transmission over other plastic films, depending on the amount and type of plasticizer used and as shown in FIG. 1. This is due to an increase in plasticizer absorption by the UHMW PVC, which enables the production of a PVC formulation containing a plasticizer in an amount above the absorption limitation of standard PVC resins in current medical products. Gas transmission may be measured using conventional means. See, for example, the method described in U.S. Pat. No. 4,280,497 to Warner et al.

Several plasticizers may be used in the present UHMW PVC resin compounds. In addition to TOTM, other candidate plasticizers include di-(2-ethylhexyl-phthalate (DEHP) and citrate ester plasticizers. Such citrate ester plasticizers include: acetyl tri-n-butyl citrate (ATBC); n-butyryl tri-n-hexyl citrate (BTHC); acetyl tri-n-octyl citrate (ATOC); and acetyl tri-n-decyl citrate (ATDC). Secondary plasticizers may be added to the UHMW PVC resin compound for compound stability. Examples of such stabilizers include epoxidized soybean oil (ESO), epoxidized linseed oil (ELO), and calcium-zinc stearates, among others.

The TOTM plasticizer extracts, or leaches out of the plastic and into the blood or blood components stored in a blood bag manufactured from such plastic, at a rate of less than about five parts per million after 7 days storage. Thus, TOTM is a preferred plasticizer over most other plasticizers. By comparison, both DEHP and BTHC plasticizers formulated in PVC compounds leach out of the plastic at a rate of about 300 to 400 parts per million for the same length of storage.

Resins currently commercially available have an absorption limit of forty-one (41%) TOTM, whereas the UHMW PVC resin compound of the present invention has an upper absorption limit of about fifty-seven (57%) TOTM. FIG. 1 illustrates the relationship between percentage TOTM and oxygen gas transmission. The horizontal axis represents percentage TOTM plasticizer in a PVC plastic film in plastic blood bags used for the collection, processing, and/or storage of blood or blood components, such as platelets. The vertical axis represents micromoles of oxygen per hour, for a standardized 350 $cm^2$ bag in room air at 22° C. As illustrated in FIG. 1, blood bags manufactured from currently available standard resins formulated with 37%–41% TOTM plasticizer have a significantly lower gas transmission than one manufactured using the UHMW resin formulated with 53% TOTM. Plastic films manufactured in accordance with the present invention preferably have an oxygen transmission rate of greater than about 18 micromoles oxygen per hour as measured across a 350 $cm^2$ film surface area. Such a value is indicated by the data reported in FIG. 1.

Because of the high gas transmission of films made using the novel UHMW PVC resin compound, such films are particularly useful in the manufacture of plastic storage bags for blood and blood components, particularly platelets. The transmission of gases, specifically oxygen, into blood helps to counter-balance changes in pH that tend to occur over time in blood stored in a closed container of blood.

Plastic films of the present invention preferably are manufactured using a PVC resin having a inherent viscosity in the range of about 1.25 to about 2.00, most preferably about 1.71. A high inherent viscosity value improves the ability of the subject resin to absorb plasticizer; the more plasticizer absorbed by the resin, the higher the gas transmission of the resulting film. This range of inherent viscosity for the UHMW PVC resins used in manufacturing the novel PVC film can be up to 80% higher than PVC films currently available, made from PVC compounds with inherent viscosities of 1.06 to 1.10.

Films may be made using the novel PVC UHMW compound by using conventional methods known and used in the industry. The percentage TOTM used in the PVC resin compositions can exceed the 41% limitation found in current PVC films, and preferably can be as high as 57% by weight based on the UHMW resin selected.

The novel films described herein may be formed into containers or other medical products, such as tubing, because they are capable of being sealed. Sealing methods that may be used in forming the novel film into products include heat, radio-frequency (RF), ultra-sonic, and chemical, among others.

Flexible plastic containers can be made from the film described herein using conventional manufacturing techniques known and used in the industry. The film is manufactured from a UHMW PVC resin having an inherent viscosity of about 1.25 or greater, preferably about 1.50 to 1.80, and most preferably about 1.71, and plasticized with about 53% TOTM plasticizer. In addition, conventionally used stabilization systems also may be added to the film PVC composition, as needed. The preferred wall thickness of blood bags manufactured using the novel PVC film may be of a conventional range of about 0.005 to about 0.025 inch, preferably about 0.012 to 0.018 inch, with 0.015 inch being the most preferred. This wall thickness results in containers having sufficient tensile strength to withstand conventional use in the collection and processing of blood and blood components. Typically, films of the plasticized PVC having the above thicknesses simply are edge sealed with appropriate fittings or are sealed using RF sealing methods.

In one embodiment, blood bags manufactured from the novel PVC film are incorporated into a multiple blood bag system, which includes various hardware, valving systems and connecting means that provide what is known as a "closed system".

As used herein, the term "closed" in reference to blood bags or blood bag systems refers to a system of multiple blood bags connected under sterile conditions via tubing and including valve devices as required to permit blood collected into one bag to be transferred into another bag without exposure to the environment outside the system. A typical "closed" system is described in U.S. Pat. No. 4,586,928 to Barnes et al.

An example of a multiple blood bag system that may include bags and other components manufactured using the novel PVC film is illustrated in FIG. 2. A multiple blood bag system 10 generally includes a donor bag 12 joined to one or more satellite bags 18, by flexible tubing 22 and a Y-connector 24. There are two satellite bags, 18a and 18b, in the illustrated example. The donor bag 12 and satellite bags 18 may have one or more access ports 16 and the donor bag 12 is equipped with a blood collection tube 14 leading to a donor needle (not shown).

In the illustrated example, one access port 16a of the donor bag 12 is connected to an additive solution bag 20. In other configurations, the donor bag 12 may be connected to other types of bags. Fluid flow through tubing 22 from bag 12 is controlled by conventional valving means located, for example, within tubing 22. Such multiple blood bag systems also may include one or more in-line integral filters 26.

In practicing the illustrated multiple blood bag system, blood may be collected into the donor bag 12 from a donor through the connected donor needle tubing 14 and then, after being centrifuged to separate the blood into desired blood components, such as red blood cells and plasma, the blood components can be processed into other bags for manufacture of blood products. Such systems 10 typically may include blood bag systems in which bags or other items (e.g. in-line filters, and the like) are "sterile docked" to other bags or tubing as described, for example in U.S. Pat. No. 4,507,119 to Spencer.

The donor bag 12 as well as satellite bags 18a and 18b and the flexible tubing 22 may be manufactured using the UHMW PVC film disclosed herein. Alternatively, any flexible polymer, such as polyethylene, may be used to manufacture the tubing.

The UHMW PVC film of the present invention may be used to manufacture blood bags and other components used in a multiple blood bag system, including flexible tubing. Additional examples of systems including in-line filters can be found in U.S. Pat. No. 4,596,657 to Wisdom, or in U.S. Pat. Nos. 4,810,378 and 5,089,146 to Carmen et al. The presence of in-line filters 26 as part of a multiple blood bag system 10 makes it possible to assure the removal of deleterious white blood cells from blood components, such as red blood cells, before the cells are stored for prolonged periods. This can also be done prior to storage of other components, such as platelets, depending on the location of the filter relative to the rest of the system.

In some multiple blood bag systems 10, a single filter may be used simply to filter the red blood cells to free them of white blood cells. In other cases, the system might include both red blood cell filters and platelet filters. Examples of this type of system can be found in U.S. Pat. No. 5,100,564 to Pall et al.

FIG. 3 illustrates a bag 30 partially cut away to show liquid contents. The bag 30 may be made from the PVC film of this invention that is single or double edge-sealed 32a, 32b (as illustrated) and includes various tubing 34 and ports 36a, 36b. The tubing 34 may include an in-line filter (not shown) and may be connected to other bags (not shown) into which the contents of the main bag 30 can be expressed after manipulation using various valves 38a, 38b as shown.

Although in a preferred embodiment of the present invention, the PVC film is described as being manufactured into plastic containers for collecting, processing, and/or storing blood and blood components, the film also may be used in the manufacture of a variety of other medical products such as tubing.

EXAMPLES

Preferred UHMW PVC resins are available from Occidental Chemical Corp., Vinyls Divisions, Dallas, Tex. under the trademarks OXY 280™, OXY 300™, OXY 320™ and OXY 410™. The TOTM plasticizer was obtained from Nuodex, Huls America, Inc., Pistcatoway, N.J. The PVC film of this example was made using conventional stabilization systems well known to those skilled in the art. (See, for example, the Warner et al. patent.) The amount of TOTM used in the following illustrative example formulation was calculated on a weight-percentage basis.

A preferred formulation for a UHMW PVC resin compound embodying the present invention is found in the following Table II:

TABLE II

| PVC Resin - UHMW | 100 phr |
| TOTM Plasticizer | 120 phr (53%) |
| Epoxized Oil | 5 phr |
| Calcium-Zinc Stabilizer | 0.32 phr |
| Mineral Oil | 0.2 phr |

Values in Table II for the components are given in the industry standard, parts per hundred resin (phr), i.e, parts component with 100 parts resin.

As shown in Table III below, film manufactured in accordance with the above UHMW PVC resin compound formulation results in oxygen transmission rates that are over twice that attainable from currently commercially available TOTM plasticized PVC blood bags. In Table III, the oxygen transmission rate for film manufactured using the novel PVC/TOTM plastic is compared with a citrate ester plasticized PVC. Some of this data is shown in bar graph form in FIG. 1.

TABLE III

Oxygen Transmission Rates of PVC in 350 cm² Films 0.15 mil thick

| | Oxygen Transmission Rate (μmoles/hr) in room air @ 22° C. |
|---|---|
| Current TOTM plasticized PVC bags | 12.9 |
| TOTM plasticized PVC bags of this invention | 27.8 |
| Citrate ester plasticized PC bags (e.g., EP 0,138,147) | 26.2 |

A bag manufactured from UHMW PVC film in accordance with the present invention is compared with conventional bags for amount of extraction into blood components stored after seven days. Table IV sets out the results of measuring the level of extraction over time of TOTM plasticizer into human plasma stored in a one liter blood bag manufactured from film of the UHMW PVC resin compound according to the present invention and having the formula found in Table I above.

TABLE IV

| One liter bag (41% TOTM control) | | | One liter bag (53% TOTM) | | |
|---|---|---|---|---|---|
| Sample ID | Day 0 | Day 7 | Sample ID | Day 0 | Day 7 |
| P101394A4 | 0.4 ppm | 0.9 ppm | P101394A | 0.6 ppm | 1.3 ppm |
| P101394A5 | 0.5 ppm | 1.0 ppm | P101394A | 0.7 ppm | 1.6 ppm |
| P101394A6 | 0.5 ppm | 1.0 ppm | P101394A | 0.7 ppm | 1.9 ppm |
| P101394B4 | 0.6 ppm | 0.8 ppm | P101394B | 0.5 ppm | 1.4 ppm |
| P101394B5 | 0.5 ppm | 1.0 ppm | P101394B | 0.6 ppm | 1.9 ppm |
| P101394B6 | 0.7 ppm | 0.9 ppm | P101394B | 0.6 ppm | 5.1 ppm |
| MEAN | 0.5 ppm | 0.9 ppm | MEAN | 0.6 ppm | 2.2 ppm |
| SD | 0.1 ppm | 0.1 ppm | SD | 0.1 ppm | 1.4 ppm |
| | | | | P = .223 | P = .084 |

After day seven, the mean extraction in parts per million is about 2.2 for bags made in accordance with this invention. In contrast, similar PVC bags plasticized with 27 wt % of DEHP or 38 wt % of BTHC extracted 430 ppm and 380 ppm after seven days, respectively.

Given the present disclosure, it is believed that numerous variations will occur to those skilled in the art. Accordingly it is intended that the above example be considered illustrative only and in no way limiting and that the scope of the invention disclosed herein should be limited only by the following claims.

We claim:

1. A flexible container for containing blood or blood components, comprising a polyvinyl chloride (PVC) film manufactured from a polyvinyl chloride compound, said compound comprising:

an ultra high molecular weight polyvinyl chloride resin having an inherent viscosity ranging from about 1.25 to about 2.00, as measured by ASTM D-1243; and about 43 to about 57 weight percent of a plasticizer.

2. The flexible container of claim 1, wherein said PVC film has a 22° C. room air oxygen transmission greater than about 18 μmoles $O_2$/hr/350 $cm^2$ film surface area.

3. A multiple blood bag system, comprising at least one said flexible container of claim 1.

4. The flexible container of claim 1, wherein said inherent viscosity is from about 1.50 to about 2.00.

5. The flexible container of claim 1, wherein the compound includes about 53 to about 57 weight percent of the plasticizer.

6. The flexible container of claim 4, wherein the compound includes about 53 to about 57 weight percent of the plasticizer.

7. The flexible container of claim 1, wherein the plasticizer is one from the group of plasticizers consisting of: tri (2-ethylhexyl) trimellitate; di-(2-ethylhexyl) phthalate; acetyl tri-n-butyl citrate; n-butyryl tri-n-hexyl citrate; acetyl tri-n-octyl citrate; and acetyl tri-n-decyl citrate.

8. The flexible container of claim 1, wherein the plasticizer comprises tri (2-ethylhexyl) trimellitate (TOTM).

9. The flexible container of claim 6, wherein the plasticizer comprises tri (2-ethylhexyl) trimellitate (TOTM).

10. The flexible container of claim 2, wherein the plasticizer comprises tri (2-ethylhexyl) trimellitate (TOTM).

11. A flexible container comprising a polyvinyl chloride film manufactured from a polyvinyl chloride compound, said polyvinyl chloride compound comprising:

an ultra high molecular weight polyvinyl chloride resin having an inherent viscosity of at least about 1.25, as measured by ASTM D-1243; and about 43 to about 57 weight percent of a plasticizer.

12. The container of claim 11, wherein the plasticizer comprises tri (2-ethylhexyl) trimellitate (TOTM).

13. The container of claim 11, wherein the inherent viscosity is at least about 1.50.

14. The container of claim 11 wherein said PVC film has a 22° C. room air oxygen transmission greater than about 18 μmoles $O_2$/hr/350 $cm^2$ film surface area.

15. The container of claim 11 wherein the plasticizer comprises di-(2-ethylhexyl) phthalate.

16. The container of claim 11 wherein the plasticizer comprises n-butyryl tri-n-hexyl citrate.

17. A method of processing blood or blood components comprising:

passing blood or blood components into a flexible container comprising a polyvinyl chloride film manufactured from a polyvinyl chloride compound, said polyvinyl chloride compound comprising an ultra high molecular weight polyvinyl chloride resin having an inherent viscosity of at least about 1.25, as measured by ASTM D-1243; and about 43 to about 57 weight percent of a plasticizer.

18. The method of claim 17, including storing platelets in the flexible container.

19. The method of claim 17, including storing the blood or blood components in the flexible container.

20. The method of claim 17 wherein said PVC film has a 22° C. room air oxygen transmission greater than about 18 μmoles $O_2$/hr/350 $cm^2$ film surface area.

* * * * *